(12) United States Patent
Prado et al.

(10) Patent No.: US 8,354,273 B2
(45) Date of Patent: Jan. 15, 2013

(54) ISOFORMS OF HUMAN SOMATOSTATIN RECEPTOR TYPE 5

(75) Inventors: Mario Durán Prado, Córdoba (ES); Antonio Jesús Martínez Fuentes, Córdoba (ES); Rafael Vazquez Martínez, Córdoba (ES); Socorro García Navarro, Córdoba (ES); María del Mar Malagón Poyato, Córdoba (ES); Justo Pastor Castaño Fuentes, Códoba (ES); Francisco Garcia-Navarro, Córdoba (ES)

(73) Assignee: Universidad de Cordoba, Córdoba (ES)

( * ) Notice: Subject to any disclaimer, the term of this patent is extended or adjusted under 35 U.S.C. 154(b) by 0 days.

(21) Appl. No.: 12/738,131

(22) PCT Filed: Oct. 17, 2007

(86) PCT No.: PCT/ES2007/000627
§ 371 (c)(1),
(2), (4) Date: May 31, 2011

(87) PCT Pub. No.: WO2009/050309
PCT Pub. Date: Apr. 23, 2009

(65) Prior Publication Data
US 2012/0003252 A1    Jan. 5, 2012

(51) Int. Cl.
*C07K 14/705* (2006.01)
*C12N 15/11* (2006.01)
*C12N 15/63* (2006.01)

(52) U.S. Cl. .................... 435/320.1; 530/350; 536/23.5
(58) Field of Classification Search .................. None
See application file for complete search history.

(56) References Cited

U.S. PATENT DOCUMENTS 6,806,054 B2 * 10/2004 Lehmann-Bruinsma et al. .............................. 435/7.1

FOREIGN PATENT DOCUMENTS

| WO | 03/072824 | 9/2003 |
| WO | 03/104816 | 12/2003 |

OTHER PUBLICATIONS

XP-002600610 Sequence for SEQ ID No. 22 of WO 03/072824.
XP-002600611 Sequence for SEQ ID No. 7 of WO 03/072824.
WO 02/061087, published Aug. 8, 2002, pp. 1-74 and pp. 240, 241 and 445 reciting SEQ ID No. 319.
WO 01/177172, published Oct. 18, 2001, pp. 1-114 and p. 266 reciting SEQ ID No. 576.

* cited by examiner

*Primary Examiner* — Michael Pak
(74) *Attorney, Agent, or Firm* — Pamela C. Ball

(57) ABSTRACT

The present invention concerns two human nucleic acids comprising sequences which code two novel isoforms of human somatostatin receptor type 5 produced by alternative adjustment, called sst5B and sst5C and with possible uses in tumoral processes. Additionally, the invention concerns oligonucleotide pairs used for the differential detection of said isoforms by means of the PCR technique in different tissues.

10 Claims, 2 Drawing Sheets

ISOFORMS OF HUMAN SOMATOSTATIN RECEPTOR TYPE 5

PURPOSE OF THE INVENTION

The present invention refers to two new isoforms of human somatostatin receptor type 5, as well as their detection in biological samples.

BACKGROUND OF THE INVENTION

The hypothalamic neuropeptide somatostatin (SRIF) acts in a multitude of organs and target tissues throughout the body, fundamentally exercising a inhibiting effect, whether over the secretion and regulation of other hormones or other diverse biological processes (Moller et al., 2003).

This action, which is generally inhibiting, but on some occasions stimulating, (Castaño et al., 1996) is exercised through a family of seven transmembrane domain (7TMD) type receptors coupled to G-proteins (GPCR), called somatostatin or ssts receptors. All ssts share a common structure consisting of an extracellular amino-terminal end connected to seven hydrophobic domains inserted into the membrane, which are in turn joined together through eight hydrophilic domains, and they end in an intracellular carboxyl-terminal end, which is important for the modulation of second messenger routes.

Up to the present, there are five different subtypes of ssts in mammals, from sst1 to sst5, and there are also two isoforms from subtype 2 (sst2A and sst2B) in mice and rats produced through alternative adjustment of the precursor messenger RNA which code two different proteins in the intracellular carboxyl-terminal region which present different properties with regard to the modulation of intracellular signaling routes. In fish, however, other isoforms from each receptor subtype have been discovered due to gene duplication phenomenon in place of other differential adjustment phenomenon of the messenger RNA that codes each of the isoforms.

The GPCRs, including the ssts, are involved in numerous medically relevant cellular processes, measured by signal transduction routes through G proteins. More specifically, one of these ssts subtypes, the human sst5 (WO 0177172, WO 0155319, WO 0136446, EP 1369698, WO 03104816) has been linked to a multitude of diverse pathologies in mammals, such as hematological and cardiovascular diseases, central and peripheral nervous system disorders, cancer, inflammatory processes, hepatic diseases, gastrointestinal and genitourinary diseases (WO 03104816).

The human somatostatin receptor type 5, sst5, is recorded in public data bases with access numbers, including but not limited to GI39756975, GI21954086, GI13937340, which contain sequences pertaining to the DNA copy of the coding sequence, as well as genomic sequences that contain the complete gene structure of said receptor, and in addition to the coding sequence, the promoter region contains intronic sequences and uncoded 5' and 3' regions. As of the present, no alternative processing of human sst5 messenger RNA has been described which brings about any different alternative isoforms other than that which is recorded in the databases and thoroughly described in the bibliography.

The sequence corresponding to messenger RNA which contains the coding sequence of the porcine sst5 receptor, as well as the uncoded 5' (GI58223147) and 3' regions, have recently been cloned (Duran et al., 2005; awaiting publication). During the cloning process of the porcine sst5 through the RACE PCR technique, partial, and then total sequences of messenger RNA variants had been obtained through alternative adjustment, which coded two new receptor isoforms, as was the case of rat sst2, but in this case, they coded six and three transmembrane domains called porcine sst5B and sst5C isoforms (p-sst5B and p-sst5C), respectively.

There is data on truncated GPCRs produced by alternative adjustment of messenger RNA, which code proteins that form structures of less than seven transmembrane domains, as has been previously described for GHRH receptors (Rekasi et al., 2000), GnRH (Pawson et al., 2005), prostaglandin (Ishii et al., 2001), etc., some of which are functional with potential relevance in tumor processes. According to the results obtained for porcine sst5, cloning of potential human homologues of the porcine sst5B and sst5C isoforms was initiated through RACE PCR, in order to subsequently evaluate their presence and significance in endocrine tumors through the PCR technique.

BIBLIOGRAPHY CITED IN THE TEXT

1. Moller L N, Stidsen C E, Hartmann B, Hoist J J. 2003. Somatostatin receptors. Biochemica et Biophysica Acta, 1616: 1-84.
2. Castaño J P, Torronteras R, Ramírez J L, Gribouval A, Sánchez-Hormigo A, Ruiz-Navarro A, Gracia-Navarro F. 1996. Somatostatin increases growth hormone (GH) secretion in a subpopulation of porcine somatotropes: evidence for functional and morphological heterogeneity among porcine GH-producing cells. Endocrinology, 137:129-136.
3. Rekasi Z, Czompoly T, Schally A V, Halmos G. 2000. Isolation and sequencing of cDNAs for splice variants of growth hormone-releasing hormone receptors from human cancers. PNAS, 97: 10561-10566.
4. Pawson A J, Maudsley S, Morgan K, Davidson L, Naor Z, Millar R. 2005. Inhibition of human type I gonadotropin-releasing hormone receptor (GnRHR-I) function by expression of a human type II GnRHR gene fragment. Endocrinology. 146(6):2639-2649.
5. Ishii Y, Sakamoto K. 2001. Suppression of protein kinase C signaling by the novel isoform for bovine PGF2a Receptor1. Biochemical and Biophysical Research Communications, 285: 1-8.
6. Landa R L, Harbeck M, Kaihara K, Chepurny O, Kitiphongspattana K, Graf O, Nikolaev V O, Lohse M J, Holz G G, Roe M W. 2005. Interplay of $Ca^{2+}$ and cAMP signaling in the insulin secreting MIN6 β-cell line. Journal of Biological Chemistry, 2; 280(35):31294-31302.
7. Vilardaga J P, Bunemann M, Krasel C, Castro M & Lohse M J. 2003. Measurement of the millisecond activation switch of G protein-coupled receptors in living cells. Nat Biotechnol 21 807-812.

DESCRIPTION OF THE INVENTION

The following concepts are detailed for the proper interpretation of the present text: A "somatostatin receptor" is a transmembrane protein coupled to a guanylate cyclase-type protein which belongs to the seven transmembrane domain type family of proteins, activated by somatostatin-type hypothalamic peptides.

"RACE-PCR" refers to Random Amplification of cDNA Ends. It entails a PCR (Polymerase Chain Reaction) based technique through which known sequence oligonucleotides are introduced within unknown sequences of cDNA, which are used as target sequences for the amplification of the cDNA region included between said oligonucleotides and the region of interest through PCR.

Hypophyseal Cushing's refers to "Cushing's Syndrome" or hypercorticism. It is a disease brought about by an increase in the production of the hormone cortisol or by the excessive use of this and other steroid hormones. Cushing's Syndrome is hypophyseal when it is due to an excessive production of adrenocorticotropic hormone by the hypophysis or pituitary gland.

The present invention includes the determination of the DNA sequence that codes two new isoforms of the human somatostatin receptor type 5 (sst5), referred to as sst5B and sst5C, with five and four transmembrane domains, respectively, brought about by an alternate adjustment of the messenger RNA contained in the genomic sequence established in the data base with access number GI13937340 (FIG. 1). Through the procedure described in the mode of executing the invention, recombinant DNA molecules are obtained which code polypeptides that exhibit the structural motifs of somatostatin receptors, at least in part of the sequence. The invention also refers to polynucleotidic DNA sequences which are hybridized with those of these new isoforms under restrictive conditions, which entails a level of homology of a least 60% between its sequences of nucleotides, preferably with 75% homology and ideally with 90% homology, or that they are derived from them through degeneration of the genetic code or by mutagenesis.

The procedure used in the invention allows functional recombinant polypeptides to be obtained for later study. Recombinant DNA is inserted into expression vectors in such a manner that they contain a sequence of nucleotides such as those described in SEQ ID 1, SEQ ID 3, SEQ ID 5, and SEQ ID 7, or derived from them. Both polypeptides expressed in expression vectors within the host cells provide a system of scrutinizing new drugs and compounds capable of joining the sst5B and sst5C isoforms in vivo and in vitro in a selective manner, as well as systems of studying the modulation of second messenger routes for each one of the isoforms in response to drugs.

As such, the invention that is the subject matter of this application refers to a purified human nucleic acid characterized by coding an isoform of the human somatostatin receptor type 5 (sst5) selected from amongst: sst5B (SEQ ID 5), sst5C (SEQ ID 7), its complementary sequence, and a sequence with at least 90% homology with the previous sequences, as well as fragments of the previous sequences.

Likewise, the invention also refers to a purified human nucleic acid which is characterized by including a partial coding sequence contained in SEQ ID 1 and SEQ ID 3.

In a specific embodiment, the invention refers to a human nucleic acid characterized by including the 3'RACE PCR fragment corresponding to sst5B, the sequence of which is SEQ ID 1, or fragments thereof. In another particular embodiment, the invention refers to a human nucleic acid characterized by including the 3'RACE PCR fragment corresponding to sst5C, the sequence of which is SEQ ID 3, or fragments thereof.

In a preferred embodiment, the invention refers to a purified polypeptide characterized by its sequence of amino acids being defined in SEQ ID 2, SEQ ID 4, SEQ ID 6, and SEQ ID 8, which is coded by one of the oligonucleotides described previously in the text.

Moreover, the invention refers to an expression vector characterized by including the nucleotide sequence described previously, which is transcriptionally coupled to an exogenous promoter. In a specific embodiment, that expression vector is characterized by said nucleotide sequence coding a polypeptide as defined previously in this text.

In a specific embodiment, the methods described above are characterized by being carried out in vitro. In a preferred embodiment, said search is carried out on complete cells. In a preferred embodiment, said method is characterized by the polypeptides detailed in SEQ ID 2, SEQ ID 4, SEQ ID 6, and SEQ ID 8 originating from an expression vector defined previously in the text. In a more preferred embodiment, said polypeptide corresponds to one of those coded by SEQ ID 1, SEQ ID 3, SEQ ID 5, SEQ ID 7, or fragments thereof.

Moreover, the invention also refers to new pairs of oligonucleotides detailed in the sequences SEQ ID 9, SEQ ID 10, SEQ ID 11, SEQ ID 12, SEQ ID 13, and SEQ ID 14, or sequences homologous to them by at least 90%, which allow the sst5 human isoforms A, B, and C to be amplified through PCR. In a specific embodiment, the invention refers to the use of said oligonucleotides for the selective amplification of the sst5A, sst5B, and sst5C isoforms through any variant of PCR. In a preferred embodiment, the invention also refers to the use of said oligonucleotides for the study of the quantitative tissular distribution of sst5A, sst5B, or sst5C in normal and tumoral tissues.

In another specific embodiment, the invention refers to a DNA copy characterized by hybridizing with the total or partial sequences contained in SEQ ID 1, SEQ ID 3, SEQ ID 5, or SEQ ID 7.

Moreover, the invention also refers to a DNA copy contained in SEQ ID 1, SEQ ID 3, SEQ ID 5, SEQ ID 7, or sequences homologous by at least 90%, characterized by being capable of silencing the gene expression of the sst5B and sst5C isoforms independently or jointly.

A specific embodiment of the present invention refers to the use of the sequences contained in SEQ ID 1, SEQ ID 3, SEQ ID 5, or SEQ ID 7 to generate selective antibodies which discriminate between the sst5B and sst5C isoforms.

The present invention also allows for the development of new drugs capable of selectively joining the new isoforms of the somatostatin receptor type 5, sst5B and sst5C, which act as agonists, antagonists, or inverse agonists by using second messenger measuring techniques such as micro-fluorometric measurement of intracellular calcium (Landa et al., 2005). More specifically, the insertion of the recombinant DNA contained in SEQ ID 1, SEQ ID 3, SEQ ID 5, and SEQ ID 7, or their derivatives, in pCDNA3 (Invitrogen) type eucaryote expression vectors, allows for the transfection of these recombinant structures in CHO-K1 or HEK-293T type tumoral cell lines, which are widely used for the study of other somatostatin receptor subtypes. The process, the methodology of which may be seen in a more detailed manner in Landa et al., (Landa et al., 2005) may be schematized in a general manner as indicated below:

(1) Cultivation of the cell line to be transfected using sterile glass slide covers.
(2) Transfection of the cellular line with the recombinant plasmid of interest.
(3) Incubation of the transfected cells with 2.5 μM of Fura-2 AM (Molecular Probes, Eugene) for 30 minutes at 37° C. in DMEM medium supplemented with 20 mM of NaHCO$_3$ at 7.4 pH.
(4) Assembly of the slide covers which the cells are adhered to in a camera coupled to an inverted microscope such as the Nikon Eclipse TE 2000 E, coupled to a Hamamatsu CCD camera (Hamamatsu Photonics, Hamamatsu), both of which are controlled with the MetaMorph and MetaFluor (Molecular Devices) software.

(5) Analysis of the transfected cells with 40× oil immersion objective through selective excitation to 340 and 380 nm and measuring the output signal to 505 nm at 5 second intervals.

(6) The changes in intracellular $Ca^{2+}$ concentration before and after the administration of the drug in question are analyzed as a quotient of the intensities of the image obtained with the respective excitation wave lengths at 340 and 380 mm by using the MetaFluor software.

The present invention also allows for the development of drugs which alter the basal state of the new isoforms of the somatostatin receptor type 5, sst5B and sst5C. In this manner, this invention would allow FRET (Fluorescence Resonance Energy Transfer) technology to be used to measure the physical interaction of both sst5B and sst5C isoforms between themselves, as well as with other proteins that belong to the GPCR family. Through this technique, changes in the receptor's basal state may be studied quickly and accurately, whether they entail aggregation or dissociation of ternary protein complexes in response to a drug. More specifically, the insertion of the recombinant DNA contained in SEQ ID 1, SEQ ID 3, SEQ ID 5, and SEQ ID 7, or their derivatives, in E-GFPN1 (Clontech) type eucaryote expression vectors, such as E-CFPN1 and E-YFPN1, would allow these recombinant structures to be cotransfected in HEK-293AD type tumoral cell lines.

The process, the methodology of which may be seen in a more detailed manner in Vilardaga et al., (Vilardaga et al., 2003) may be schematized in a general manner as indicated below:

(1) Cultivation of the cell line to be transfected using sterile glass slide covers.
(2) Cotransfection of the cell line with the recombinant plasmids of interest.
(3) Assembly of the slide covers which the cells are adhered to in a camera coupled to an inverted microscope such as the Nikon Eclipse TE 2000 E, coupled to a Hamamatsu CCD camera (Hamamatsu Photonics, Hamamatsu), both of which are controlled with the MetaMorph and MetaFluor (Molecular Devices) software.
(4) Analysis of the transfected cells with 40× oil immersion objective through selective excitation to 440 and 495 nm and measuring the signal to 510 and 540 nm, respectively, at 5 second intervals.
(5) The changes in the intensity of the signal of both fluorescent molecules before and after the administration of the drug in question are analyzed as a quotient of the intensities of the image obtained with the respective excitation wave lengths at 510 and 540 nm by using the MetaFluor software.

MODES OF EXECUTING THE INVENTION

An example is described below for greater illustration of the invention, but does not limit it in any way.

Example

Figure 1:
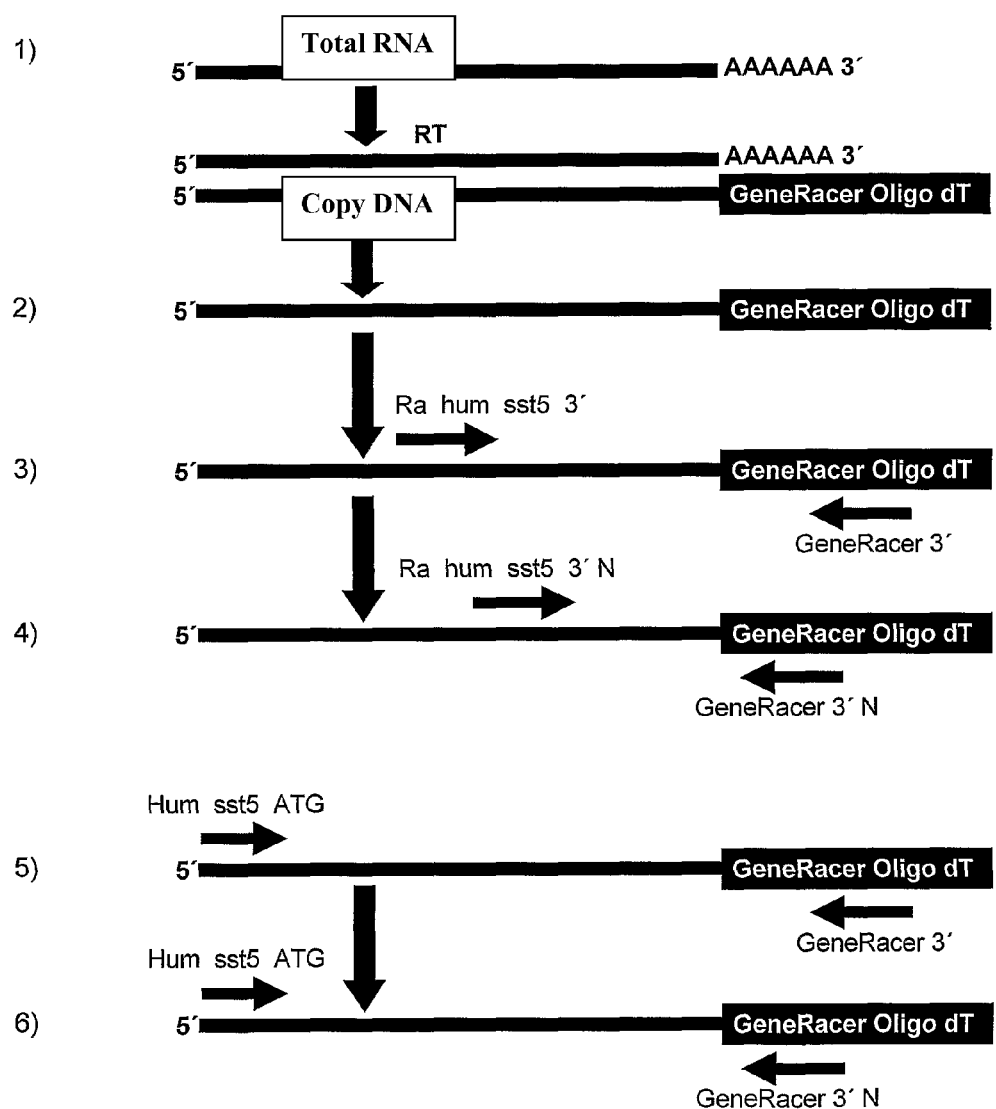
FIG. 1: Amplification drawing of partial sequences corresponding to the sst5B and sst5C isoforms through the 3'RACE PCR technique. The stages described in the text are presented and the oligonucleotides used in each case are displayed according to the nomenclature of Table 1.

The following stages described in FIG. 1 were followed to clone partial sequences of the sst5B and sst5C isoforms:
(1) Total isolation and retrotranscription of RNA of various tumoral tissues.
(2) Amplification of 3' region of the sst5B and sst5C isoforms through RACE PCR; and
(3) reamplification using oligonucleotides nested in those used in step (2).
(4) Cloning the PCR products from step (3) and sequencing to determine their proper sequence.
(5) Verification of the initiation of transcription of the sst5B and sst5C isoforms through PCR using the DNA copy created in (1) as a template.
(6) Reamplification of (5) in order to verify the specificity of the PCR bands obtained in that step.

The described amplification method was carried out by following the indications of the Invitrogen® Life Technologies "GeneRacer® Kit", except for steps (5) and (6).

Figure 2:
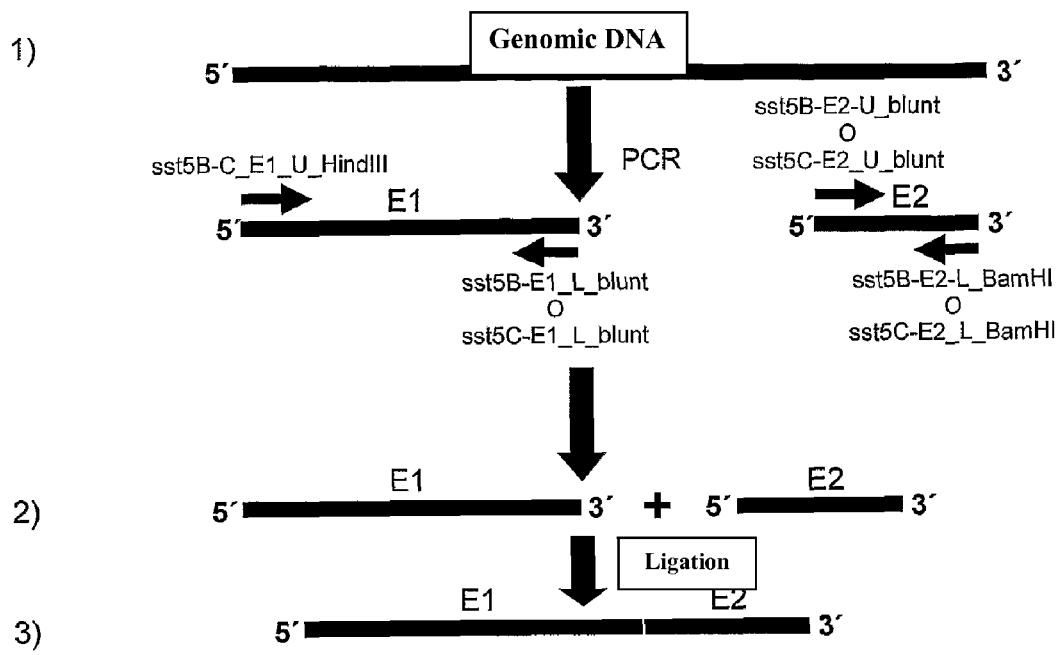
FIG. 2: Amplification drawing of coding sequences of the sst5B and sst5C isoforms through the PCR amplification technique and triple ligation. The stages described in the text are presented and the oligonucleotides used in each case are displayed according to the nomenclature of Table 1.

The strategy schematized in FIG. 2 was used to clone the coding sequences and functional expression of the sst5B and sst5C isoforms:
(1) Both exon 1 (E1) and exon 2 (E2) corresponding to each of the isoforms were amplified from human genomic DNA.
(2) Enzymatic digestion of the PCR fragments, and
(3) Mutual ligation of exons E1 and E2 within an expression vector (not shown in the drawing).

In addition, pairs of oligonucleotides were designed capable of discriminating each of the sst5A, sst5B, and sst5C isoforms (SEQ ID 9 to SEQ ID 14) and which can be used for quantitative purposes, selectively discriminating each isoform under the specific PCR conditions detailed further along in the text.

Isolation of Nucleic Acids.

Isolation of RNA. This was carried out by using the reagent Trizol from Invitrogen® according to the recommendations indicated by that company. Tissues from two hypophyseal adenomas diagnosed as non-functioning and a sample of hypophyseal "Cushing's" were used as starting material for the total isolation of RNA designated for cloning. The resulting RNA was resuspended in a final volume of 12 µl of DEPC-treated $H_2O$, of which 1 µl was used for spectrophotometric quantification. 2 µg of RNA from each of the tumors was used for retrotranscription in a final volume of 20 µl. RNA from the HeLa tumoral cell line from the "GeneRacer kit" was also used, and the same quantity of RNA was used for the retrotranscription reaction (FIG. 1.1). The indications from the Invitrogen® "GeneRacer® kit" were followed for the retrotranscription reaction. A heterogeneous battery of hypophyseal tumoral tissues was also used for diagnostic purposes, from which a quantity of between 15 and 100 mg was used for the extraction of total RNA. The resulting RNA was also resuspended in a final volume of 12 µl of DEPC-treated $H_2O$, of which 1 µl was used for spectrophotometric quantification. Between 2 and 5 µg of RNA from each of the tumors, according to the yield of each extraction, was used for retrotranscription. The retrotranscription reaction was carried out in a total volume of 20 µl using the BD Biosciences "PowerScript" enzyme according to the manufacturer's indications.

Isolation of DNA. This was carried out using the reagent Trizol from Invitrogen®, using $10^7$ human lymphocytes as the starting material. The genomic DNA obtained was quantified spectrophotometrically.

Amplification by PCR and Obtaining Partial Sequences of the sst5B and sst5C Isoforms.

As indicated previously, the "GeneRacer® Kit" commercial amplification system from Invitrogen® was used in combination with the specifically designed oligonucleotides indicated in Table 1.

observed in 1% agarose gel and the bands obtained were purified by using the QuiaQuick Mini Elute (Quiagen) commercial kit. The PCR products purified in this manner were cloned with blunt ends in the EcoRV restriction site of the pBluescript KSII+ vector and were sequenced, resulting in the sequence corresponding to 609 pairs of bases (SEQ ID 1) obtained from the DNA copy of HeLa cells and another sequence of 197 base pairs (SEQ ID 3) obtained from the DNA copy from the hypophyseal "Cushing's". Both DNA copies obtained from the HeLa cells and the hypophyseal

TABLE 1

Oligonucleotides used for selective amplification of partial sequences of h-sst5B and h-sst5C.

| Name (SEQ ID) | 5'→3' sequence, position in sequence of reference and amino acids sequence | Reading direction | Reference |
|---|---|---|---|
| Hum_sst5_ATG (15) | 1-ATGGAGCCCCTGTTCCCAGCCT-22<br>1-MEPLFPA-7 | Sense | GI39756975 |
| Ra_hum_sst5_3' (16) | 490-TGGGTCCTGTCTCTGTGCATGTC-512<br>164-WVLSLCM-170 | Sense | GI39756975 |
| Ra_hum_sst5_3'N (17) | 523-CTGGTGTTCGCGGACGTGCAG-543<br>175-LVFADVQ-181 | Sense | GI39756975 |
| sst5B-C_E1_U_HindIII (18) | 1-*TCAAGCTT*CGATGGAGCCCCTGTTCCCAGC-20<br>1-MEPLFP-6 | Sense | GI39756975 |
| sst5B-E1_L_blunt (19) | 599-CGGCGCGAAGAAGCCCAGCAC-619<br>207-VLGFFAP-213 | Anti-sense | GI39756975 |
| sst5B-E2-U_blunt (20) | 2275-CTGCTGAGAGGCAGCGGCC-2293<br>LLRGSG | Sense | GI13937340 |
| sst5B-E2-L_BamHI (21) | 2437-*TTAGGATCC*TCAGAGCAAGGCCAAGTTGCC-2457<br>GNLALL | Anti-sense | GI13937340 |
| sst5C-E1_L_blunt (22) | 675-GTTGCAGGTACCGCCCTCCTG-695<br>181-QEGGTCN-187 | Anti-sense | GI39756975 |
| sst5C-E2_U_blunt (23) | 2548-CGTCTGCCCAGAGCAGGACCTC-2569<br>RLPRAGP | Sense | GI13937340 |
| sst5C-E2_L_BamHI (24) | 2617-*ACTGGATCC*TCAGCCTGGGCCTTTCTCCTG-2637<br>QEKGPG | Sense | GI13937340 |

*The bases appearing in italics represent restriction enzyme targets.

After the retrotranscription reaction, 100 ng of DNA copy was used for each PCR reaction, using the Ra_hum_sst5_3' (SEQ ID 16) and GeneRacer 3' oligonucleotides (FIG. 1.3), in which the samples underwent an initial 2 minute denaturation at 94° C., followed by five 30 second repetitions of denaturation at 94° C. and 1 minute 30 seconds of alignment and extension at 72° C., in addition to another thirty-five cycles equal to the previous one but using the less astringent alignment temperature of 66° C. The amplification program continued with 7 minutes of extension at 72° C. in order to finalize the synthesis of incomplete PCR products. 1 µl from each PCR product was reamplified with the Ra_hum_sst5_3'N (SEQ ID 17) and GeneRacer 3'N nested oligonucleotides (FIG. 1.4), with the samples undergoing an initial 2 minute denaturation at 94° C., and then thirty-two 30 second denaturation cycles at 94° C., 30 seconds of alignment at 66° C., and 40 seconds of extension at 72° C. The amplification program continued with 7 minutes of extension at 72° C. in order to finalize the synthesis of incomplete PCR products. A mixture of Biotools Certamp polymerases provided with a plug specifically for complex mixtures was used for both amplifications. The different PCR reactions were carried out with all DNA copies concurrently. The PCR products were "Cushing's" were then amplified with the Hum_sst5_ATG (SEQ ID 15) and GeneRacer 3' oligonucleotides (FIG. 1.5) and the products of those reactions were reamplified with the same Hum_sst5_ATG oligonucleotide and the GeneRacer 3'N nested oligonucleotide (FIG. 1.6). The same program was used for both PCR amplification reactions consisting of an initial 2 minute denaturation at 94° C. followed by forty 30 second denaturation cycles at 94° C., 30 seconds of alignment at 62° C., and 1 minute 30 seconds of extension at 72° C. Observation in 1% agarose gel allowed the existence of a band of around 1 kilobase obtained from the DNA copy of HeLa, and another band of around 700 base pairs obtained from the DNA copy of the hypophyseal "Cushing's", to be proven. This result allowed it to be proven that, analogously to the homologous porcine sequences, both isoforms, referred to as sst5B and sst5C, respectively, share a putative beginning from the common translation with the sst5A isoform, the sequence of which was previously known and available in the databases with access number GI39756975.

Obtaining the Coding Sequences Corresponding to the sst5B and sst5C Isoforms.

A strategy based on the independent amplification of the two exons that comprise each isoform (FIG. 2), as well as the subsequent ligation of both fragments within a eucaryote expression vector, was followed for the cloning and functional expression of the sst5B and sst5C isoforms. More specifically, starting from genomic DNA as a template, exon 1 (E1) in each isoform was amplified through PCR, using a common sense oligonucleotide for sst5B and sst5C, sst5B-C_E1_U_HindIII (SEQ ID 18), which incorporates a sequence of restriction for the HindIII enzyme, and an antisense oligonucleotide specific to each isoform, sst5B-E1_L_blunt (SEQ ID 19) and sst5C-E1_L_blunt (SEQ ID 22) for sst5B and sst5C, respectively (FIGS. 2.1 and 3.2). Exons 2 (E2) were amplified in an analogous manner, with the specific pairs of sense and antisense oligonucleotides sst5B-E2-U_blunt (SEQ ID 20)/sst5B-E2_L_BamHI (SEQ ID 21) for isoform sst5B and sst5C-E2_U_blunt (SEQ ID 23)/sst5C-E2_L_BamHI (SEQ ID 24) for isoform sst5C. The four PCR reactions were carried out concurrently using a program consisting of an initial 2 minute denaturation at 94° C. followed by thirty-four 30 second denaturation cycles at 94° C., 30 seconds of alignment at 62° C., and 40 seconds of extension at 72° C. In every case, a high-fidelity polymerase was used with a Pfu Ultra (Stratagene) type copy supplementing the reactions with 1M betaine (Sigma). Through these PCR reactions, a sequence of restriction for the HindIII enzyme was able to be incorporated into the 5' end of each E1, the 3' blunt end of the E1, the 5' blunt end of the E2, and a sequence of restriction for the BamHI enzyme in the 3' end of each E2. It was previously verified that none of the enzymes of restriction had additional cut sites within the sequences of interest. The PCR fragments obtained were purified by using the QuiaQuick Mini Elute (Quiagen) commercial kit, and after enzymatic digestion with HindIII and BamHI, they were linked through a triple reaction within the pCDNA3+ (Invitrogen) eucaryote expression vector which had been linearized with the previous enzymes of restriction. Both sst5B-pCDNA3+ and sst5C-pCDNA3+ structures were sequenced at least in duplicate in order to verify the integrity of the sequences and to compare them with the GI13937340 genomic sequence, which contains the two isoforms, by using the BLAST 2 SEQUENCES program http://www.ncbi.nlm.nih.gov/blast/bl2seq/wblast2.cgi.

Selective Differential Amplification of Partial Sequences Corresponding to the sst5A, sst5B, and sst5C Isoforms for Qualitative Purposes.

Pairs of oligonucleotides were developed for diagnostic purposes, which allow selective discrimination by PCR of each of the human sst5, sst5A (GI39756975), sst5B, and sst5C isoforms. The pair of oligonucleotides Hum_sst5A_cuant_U/Hum_sst5A_cuant_L, SEQ ID 9 and SEQ ID 10, respectively, amplify a PCR product of 154 base pairs using an alignment temperature of 68° C. The pair of oligonucleotides Hum_sst5B_cuant_U/Hum_sst5B_cuant_L, SEQ ID 11 and SEQ ID 12, respectively, amplify a PCR fragment of 142 base pairs, using an alignment temperature of 68° C., contained in the sequence corresponding to sst5B (SEQ ID 5) and does not amplify the sst5C or sst5A (GI39756975) isoforms, while it produces an amplification product of 1643 base pairs contained in the GI13937340 human genomic sequence which includes the intron situated between exons E1 and E2 of the sst5B isoform. The pair of oligonucleotides Hum_sst5C_cuant_U/Hum_sst5C_cuant_L, SEQ ID 13 and SEQ ID 14, respectively, amplify a PCR fragment of 137 base pairs using an alignment temperature of 68° C., contained in the sequence corresponding to sst5C (SEQ ID 6) and also amplify a fragment of 488 base pairs contained in the sequence corresponding to the sst5B and another fragment of 1989 base pairs contained in the human genomic sequence GI13937340, which includes the intron situated between exons E1 and E2 of the isoform sst5C. The three PCR reactions are carried out concurrently using a common PCR program consisting of an initial 2 minute denaturation at 94° C. and 37 10 second repetitions at 94° C., 10 seconds of alignment at 68° C. and 10 seconds of extension at 72° C. By using these PCR conditions, each pair of oligonucleotides only amplifies the specific PCR fragment of each isoform selectively, without amplifying the other additional sequences mentioned previously. In every case, the reactions were supplemented with 1M betaine (Sigma). This methodology allowed the selective presence of the sst5B isoform to be observed in various hypophyseal tumors clinically classified as non-functioning.

The invention claimed is:

1. A purified somatostatin receptor type 5 nucleic acid, fragment or homolog, wherein said purified somatostatin receptor type 5 nucleic acid, fragment or homolog is at least 90% identical to SEQ ID NO:5, SEQ ID NO:7, SEQ ID NO:1, SEQ ID NO:3, or fully complementary nucleic acids thereof.

2. A purified somatostatin receptor type 5 nucleic acid according to claim 1, wherein said purified nucleic acid, fragment, or homolog is SEQ ID NO:5, SEQ ID NO:7, SEQ ID NO:1, SEQ ID NO:3, or fully complementary nucleic acids thereof.

3. A purified somatostatin receptor type 5 polypeptide, fragment or homolog thereof, wherein said purified somatostatin receptor type 5 polypeptide, fragment or homolog is at least 90% identical to SEQ ID NO:2, SEQ ID NO:4, SEQ ID NO:6 or SEQ ID NO:8.

4. A purified somatostatin receptor type 5 polypeptide, fragment or homolog thereof according to claim 3, wherein said purified somatostatin receptor type 5 polypeptide, fragment or homolog is SEQ ID NO:2, SEQ ID NO:4, SEQ ID NO:6 or SEQ ID NO:8.

5. A purified somatostatin receptor type 5 polypeptide according to claim 4, wherein said polypeptide is SEQ ID NO:2 or SEQ ID NO:4.

6. A purified somatostatin receptor type 5 polypeptide according to claim 4, wherein said polypeptide is SEQ ID NO:6 or SEQ ID NO:8.

7. An isolated expression vector comprising a somatostatin receptor type 5 nucleic acid, fragment, or homolog according to claim 1.

8. An expression vector according to claim 7, wherein said somatostatin receptor type 5 nucleic acid, fragment or homolog is SEQ ID NO:1, SEQ ID NO:3, SEQ ID NO:5 or SEQ ID NO:7, or fully complementary nucleic acids thereof.

9. An expression vector according to claim 8, wherein said somatostatin receptor type 5 nucleic acid, fragment or homolog is SEQ ID NO:1, or a fully complementary nucleic acid thereof.

10. An expression vector according to claim 8, wherein said somatostatin receptor type 5 nucleic acid, fragment or homolog is SEQ ID NO:3, or a fully complementary nucleic acid thereof.

* * * * *

SEQUENCE LISTING

```
<160> NUMBER OF SEQ ID NOS: 24

<210> SEQ ID NO 1
<211> LENGTH: 609
<212> TYPE: DNA
<213> ORGANISM: Homo sapiens
<220> FEATURE:
<221> NAME/KEY: CDS
<222> LOCATION: (1)..(333)
<220> FEATURE:
<221> NAME/KEY: 3'UTR
<222> LOCATION: (334)..(609)

<400> SEQUENCE: 1 tgg gtc ctg tct ctg tgc atg tcg ctg ccg ctc ctg gtg ttc gcg gac      48
Trp Val Leu Ser Leu Cys Met Ser Leu Pro Leu Leu Val Phe Ala Asp
1               5                   10                  15 gtg cag gag ggc ggt acc tgc aac gcc agc tgg ccg gag ccc gtg ggg      96
Val Gln Glu Gly Gly Thr Cys Asn Ala Ser Trp Pro Glu Pro Val Gly
            20                  25                  30 ctg tgg ggc gcc gtc ttc atc atc tac acg gcc gtg ctg ggc ttc ttc    144
Leu Trp Gly Ala Val Phe Ile Ile Tyr Thr Ala Val Leu Gly Phe Phe
```

```
                      35                  40                  45
gcg ccg ctg ctg aga ggc agc ggc cgc gcg ggt gac gca aat ggc agg        192
Ala Pro Leu Leu Arg Gly Ser Gly Arg Ala Gly Asp Ala Asn Gly Arg
 50                  55                  60 ccc tgg gaa tcc cgc cgc ctc cca cct aga att gtc cta cct ccc cca        240
Pro Trp Glu Ser Arg Arg Leu Pro Pro Arg Ile Val Leu Pro Pro Pro
 65                  70                  75                  80 ccc caa aca cca gct ttt cct ggc gcc cca ggc cca gaa cgt ggg ccc        288
Pro Gln Thr Pro Ala Phe Pro Gly Ala Pro Gly Pro Glu Arg Gly Pro
                 85                  90                  95 aga gag cct tgc tgg ggt ctc tgg ggc aac ttg gcc ttg ctc tga            333
Arg Glu Pro Cys Trp Gly Leu Trp Gly Asn Leu Ala Leu Leu
                100                 105                 110 ggctggaagg agaaggacca gggtgcggca tcactcggcc tcaggga ccc ctctgccctg     393 cccagcactg gccccgaccc gtgctcccgc cgtctgccca gagcaggacc tcaacctcct     453
ggagggcaca gggagcggct gagtgggcac aaatcctggc aggagaaagg cccaggctga     513
ggccaggcct gggaaacatc caagcagtga ggacacgcgt gtttgacaac tgctcccctg     573
aataaatgcg aggataaatg tttaaaaaaa aaaaaa                               609

<210> SEQ ID NO 2
<211> LENGTH: 110
<212> TYPE: PRT
<213> ORGANISM: Homo sapiens

<400> SEQUENCE: 2

Trp Val Leu Ser Leu Cys Met Ser Leu Pro Leu Leu Val Phe Ala Asp
 1               5                  10                  15

Val Gln Glu Gly Gly Thr Cys Asn Ala Ser Trp Pro Glu Pro Val Gly
                20                  25                  30

Leu Trp Gly Ala Val Phe Ile Ile Tyr Thr Ala Val Leu Gly Phe Phe
             35                  40                  45

Ala Pro Leu Leu Arg Gly Ser Gly Arg Ala Gly Asp Ala Asn Gly Arg
 50                  55                  60

Pro Trp Glu Ser Arg Arg Leu Pro Pro Arg Ile Val Leu Pro Pro Pro
 65                  70                  75                  80

Pro Gln Thr Pro Ala Phe Pro Gly Ala Pro Gly Pro Glu Arg Gly Pro
                 85                  90                  95

Arg Glu Pro Cys Trp Gly Leu Trp Gly Asn Leu Ala Leu Leu
                100                 105                 110

<210> SEQ ID NO 3
<211> LENGTH: 197
<212> TYPE: DNA
<213> ORGANISM: Homo sapiens
<220> FEATURE:
<221> NAME/KEY: CDS
<222> LOCATION: (1)..(162)
<220> FEATURE:
<221> NAME/KEY: 3'UTR
<222> LOCATION: (163)..(197)

<400> SEQUENCE: 3 tgg gtc ctg tct ctg tgc atg tcg ctg ccg ctc ctg gtg ttc gcg gac        48
Trp Val Leu Ser Leu Cys Met Ser Leu Pro Leu Leu Val Phe Ala Asp
 1               5                  10                  15 gtg cag gag ggc ggt acc tgc aac cgt ctg ccc aga gca gga cct caa        96
Val Gln Glu Gly Gly Thr Cys Asn Arg Leu Pro Arg Ala Gly Pro Gln
                20                  25                  30 cct cct gga ggg cac agg gag cgg ctg agt ggg cac aaa tcc tgg cag       144
```

```
Pro Pro Gly Gly His Arg Glu Arg Leu Ser Gly His Lys Ser Trp Gln
        35                  40                  45 gag aaa ggc cca ggc tga ggccaggcct gggaaacatg ttaaaaaaaa aaaaa       197
Glu Lys Gly Pro Gly
        50

<210> SEQ ID NO 4
<211> LENGTH: 53
<212> TYPE: PRT
<213> ORGANISM: Homo sapiens

<400> SEQUENCE: 4

Trp Val Leu Ser Leu Cys Met Ser Leu Pro Leu Leu Val Phe Ala Asp
1               5                   10                  15

Val Gln Glu Gly Gly Thr Cys Asn Arg Leu Pro Arg Ala Gly Pro Gln
            20                  25                  30

Pro Pro Gly Gly His Arg Glu Arg Leu Ser Gly His Lys Ser Trp Gln
        35                  40                  45

Glu Lys Gly Pro Gly
        50

<210> SEQ ID NO 5
<211> LENGTH: 822
<212> TYPE: DNA
<213> ORGANISM: Homo sapiens
<220> FEATURE:
<221> NAME/KEY: CDS
<222> LOCATION: (1)..(822)

<400> SEQUENCE: 5 atg gag ccc ctg ttc cca gcc tcc acg ccc agc tgg aac gcc tcc tcc       48
Met Glu Pro Leu Phe Pro Ala Ser Thr Pro Ser Trp Asn Ala Ser Ser
1               5                   10                  15 ccg ggg gct gcc tct gga ggc ggt gac aac agg acg ctg gtg ggg ccg       96
Pro Gly Ala Ala Ser Gly Gly Gly Asp Asn Arg Thr Leu Val Gly Pro
            20                  25                  30 gcg ccc tcg gca ggg ccc cgg gcg gtg ctg gtg ccc gtg ctg tac ctg      144
Ala Pro Ser Ala Gly Ala Arg Ala Val Leu Val Pro Val Leu Tyr Leu
        35                  40                  45 ctg gtg tgt gcg gcc ggg ctg gtc ggg aac acg ctg gtc atc tac gtg      192
Leu Val Cys Ala Ala Gly Leu Val Gly Asn Thr Leu Val Ile Tyr Val
    50                  55                  60 gtg ctg cgc ttc gcc aag atg aag acc gtc acc aac atc tac att ctc      240
Val Leu Arg Phe Ala Lys Met Lys Thr Val Thr Asn Ile Tyr Ile Leu
65                  70                  75                  80 aac ctg gca gtg gcc gac gtc ctg tac atg ctg ggg ctg cct ttc ctg      288
Asn Leu Ala Val Ala Asp Val Leu Tyr Met Leu Gly Leu Pro Phe Leu
                85                  90                  95 gcc acg cag aac gcc gcg tcc ttc tgg ccc ttc ggc ccc gtc ctg tgc      336
Ala Thr Gln Asn Ala Ala Ser Phe Trp Pro Phe Gly Pro Val Leu Cys
            100                 105                 110 cgc ctg gtc atg acg ctg gac ggc gtc aac cag ttc acc agt gtc ttc      384
Arg Leu Val Met Thr Leu Asp Gly Val Asn Gln Phe Thr Ser Val Phe
        115                 120                 125 tgc ctg aca gtc atg agc gtg gac cgc tac ctg gca gtg gtg cac ccg      432
Cys Leu Thr Val Met Ser Val Asp Arg Tyr Leu Ala Val Val His Pro
    130                 135                 140 ctg agc tcg gcc cgc tgg cgc cgc ccg cgt gtg gcc aag ctg gcg agc      480
Leu Ser Ser Ala Arg Trp Arg Arg Pro Arg Val Ala Lys Leu Ala Ser
145                 150                 155                 160 gcc gcg gcc tgg gtc ctg tct ctg tgc atg tcg ctg ccg ctc ctg gtg      528
Ala Ala Ala Trp Val Leu Ser Leu Cys Met Ser Leu Pro Leu Leu Val
```

```
                            165                 170                 175
ttc gcg gac gtg cag gag ggc ggt acc tgc aac gcc agc tgg ccg gag     576
Phe Ala Asp Val Gln Glu Gly Gly Thr Cys Asn Ala Ser Trp Pro Glu
            180                 185                 190 ccc gtg ggg ctg tgg ggc gcc gtc ttc atc atc tac acg gcc gtg ctg     624
Pro Val Gly Leu Trp Gly Ala Val Phe Ile Ile Tyr Thr Ala Val Leu
        195                 200                 205 ggc ttc ttc gcg ccg ctg ctg aga ggc agc ggc cgc gcg ggt gac gca     672
Gly Phe Phe Ala Pro Leu Leu Arg Gly Ser Gly Arg Ala Gly Asp Ala
    210                 215                 220 aat ggc agg ccc tgg gaa tcc cgc cgc ctc cca cct aga att gtc cta     720
Asn Gly Arg Pro Trp Glu Ser Arg Arg Leu Pro Pro Arg Ile Val Leu
225                 230                 235                 240 cct ccc cca ccc caa aca cca gct ttt cct ggc gcc cca ggc cca gaa     768
Pro Pro Pro Pro Gln Thr Pro Ala Phe Pro Gly Ala Pro Gly Pro Glu
                245                 250                 255 cgt ggg ccc aga gag cct tgc tgg ggt ctc tgg ggc aac ttg gcc ttg     816
Arg Gly Pro Arg Glu Pro Cys Trp Gly Leu Trp Gly Asn Leu Ala Leu
            260                 265                 270 ctc tga                                                             822
Leu

<210> SEQ ID NO 6
<211> LENGTH: 273
<212> TYPE: PRT
<213> ORGANISM: Homo sapiens

<400> SEQUENCE: 6

Met Glu Pro Leu Phe Pro Ala Ser Thr Pro Ser Trp Asn Ala Ser Ser
1               5                   10                  15

Pro Gly Ala Ala Ser Gly Gly Gly Asp Asn Arg Thr Leu Val Gly Pro
            20                  25                  30

Ala Pro Ser Ala Gly Ala Arg Ala Val Leu Val Pro Val Leu Tyr Leu
        35                  40                  45

Leu Val Cys Ala Ala Gly Leu Gly Gly Asn Thr Leu Val Ile Tyr Val
    50                  55                  60

Val Leu Arg Phe Ala Lys Met Lys Thr Val Thr Asn Ile Tyr Ile Leu
65                  70                  75                  80

Asn Leu Ala Val Ala Asp Val Leu Tyr Met Leu Gly Leu Pro Phe Leu
                85                  90                  95

Ala Thr Gln Asn Ala Ala Ser Phe Trp Pro Phe Gly Pro Val Leu Cys
            100                 105                 110

Arg Leu Val Met Thr Leu Asp Gly Val Asn Gln Phe Thr Ser Val Phe
        115                 120                 125

Cys Leu Thr Val Met Ser Val Asp Arg Tyr Leu Ala Val Val His Pro
    130                 135                 140

Leu Ser Ser Ala Arg Trp Arg Arg Pro Arg Val Ala Lys Leu Ala Ser
145                 150                 155                 160

Ala Ala Ala Trp Val Leu Ser Leu Cys Met Ser Leu Pro Leu Leu Val
                165                 170                 175

Phe Ala Asp Val Gln Glu Gly Gly Thr Cys Asn Ala Ser Trp Pro Glu
            180                 185                 190

Pro Val Gly Leu Trp Gly Ala Val Phe Ile Ile Tyr Thr Ala Val Leu
        195                 200                 205

Gly Phe Phe Ala Pro Leu Leu Arg Gly Ser Gly Arg Ala Gly Asp Ala
    210                 215                 220

Asn Gly Arg Pro Trp Glu Ser Arg Arg Leu Pro Pro Arg Ile Val Leu
```

```
                    225                 230                 235                 240

Pro Pro Pro Pro Gln Thr Pro Ala Phe Pro Gly Ala Pro Gly Pro Glu
                             245                 250                 255

Arg Gly Pro Arg Glu Pro Cys Trp Gly Leu Trp Gly Asn Leu Ala Leu
                     260                 265                 270

Leu

<210> SEQ ID NO 7
<211> LENGTH: 651
<212> TYPE: DNA
<213> ORGANISM: Homo sapiens
<220> FEATURE:
<221> NAME/KEY: CDS
<222> LOCATION: (1)..(651)

<400> SEQUENCE: 7 atg gag ccc ctg ttc cca gcc tcc acg ccc agc tgg aac gcc tcc tcc        48
Met Glu Pro Leu Phe Pro Ala Ser Thr Pro Ser Trp Asn Ala Ser Ser
  1               5                  10                  15 ccg ggg gct gcc tct gga ggc ggt gac aac agg acg ctg gtg ggg ccg        96
Pro Gly Ala Ala Ser Gly Gly Gly Asp Asn Arg Thr Leu Val Gly Pro
             20                  25                  30 gcg ccc tcg gca ggg gcc cgg gcg gtg ctg gtg ccc gtg ctg tac ctg       144
Ala Pro Ser Ala Gly Ala Arg Ala Val Leu Val Pro Val Leu Tyr Leu
         35                  40                  45 ctg gtg tgt gcg gcc ggg ctg gcc ggg aac acg ctg gtc atc tac gtg       192
Leu Val Cys Ala Ala Gly Leu Ala Gly Asn Thr Leu Val Ile Tyr Val
     50                  55                  60 gtg ctg cgc ttc gcc aag atg aag acc gtc acc aac atc tac att ctc       240
Val Leu Arg Phe Ala Lys Met Lys Thr Val Thr Asn Ile Tyr Ile Leu
 65                  70                  75                  80 aac ctg gca gtg gcc gac gtc ctg tac atg ctg ggg ctg cct ttc ctg       288
Asn Leu Ala Val Ala Asp Val Leu Tyr Met Leu Gly Leu Pro Phe Leu
                 85                  90                  95 gcc acg cag aac gcc gcg tcc ttc tgg ccc ttc ggc ccc gtc ctg tgc       336
Ala Thr Gln Asn Ala Ala Ser Phe Trp Pro Phe Gly Pro Val Leu Cys
            100                 105                 110 cgc ctg gtc atg acg ctg gac ggc gtc aac cag ttc acc agt gtc ttc       384
Arg Leu Val Met Thr Leu Asp Gly Val Asn Gln Phe Thr Ser Val Phe
        115                 120                 125 tgc ctg aca gtc atg agc gtg gac cgc tac ctg gca gtg gtg cac ccg       432
Cys Leu Thr Val Met Ser Val Asp Arg Tyr Leu Ala Val Val His Pro
    130                 135                 140 ctg agc tcg gcc cgc tgg cgc cgc ccg cgt gtg gcc aag ctg gcg agc       480
Leu Ser Ser Ala Arg Trp Arg Arg Pro Arg Val Ala Lys Leu Ala Ser
145                 150                 155                 160 gcc gcg gcc tgg gtc ctg tct ctg tgc atg tcg ctg ccg ctc ctg gtg       528
Ala Ala Ala Trp Val Leu Ser Leu Cys Met Ser Leu Pro Leu Leu Val
                165                 170                 175 ttc gcg gac gtg cag gag ggc ggt acc tgc aac cgt ctg ccc aga gca       576
Phe Ala Asp Val Gln Glu Gly Gly Thr Cys Asn Arg Leu Pro Arg Ala
            180                 185                 190 gga cct caa cct cct gga ggg cac agg gag cgg ctg agt ggg cac aaa       624
Gly Pro Gln Pro Pro Gly Gly His Arg Glu Arg Leu Ser Gly His Lys
        195                 200                 205 tcc tgg cag gag aaa ggc cca ggc tga                                   651
Ser Trp Gln Glu Lys Gly Pro Gly
    210                 215

<210> SEQ ID NO 8
<211> LENGTH: 216
```

```
<212> TYPE: PRT
<213> ORGANISM: Homo sapiens

<400> SEQUENCE: 8

Met Glu Pro Leu Phe Pro Ala Ser Thr Pro Ser Trp Asn Ala Ser Ser
1               5                   10                  15

Pro Gly Ala Ala Ser Gly Gly Asp Asn Arg Thr Leu Val Gly Pro
            20                  25                  30

Ala Pro Ser Ala Gly Ala Arg Ala Val Leu Val Pro Val Leu Tyr Leu
            35                  40                  45

Leu Val Cys Ala Ala Gly Leu Gly Gly Asn Thr Leu Val Ile Tyr Val
        50                  55                  60

Val Leu Arg Phe Ala Lys Met Lys Thr Val Thr Asn Ile Tyr Ile Leu
65                  70                  75                  80

Asn Leu Ala Val Ala Asp Val Leu Tyr Met Leu Gly Leu Pro Phe Leu
                85                  90                  95

Ala Thr Gln Asn Ala Ala Ser Phe Trp Pro Phe Gly Pro Val Leu Cys
            100                 105                 110

Arg Leu Val Met Thr Leu Asp Gly Val Asn Gln Phe Thr Ser Val Phe
        115                 120                 125

Cys Leu Thr Val Met Ser Val Asp Arg Tyr Leu Ala Val Val His Pro
130                 135                 140

Leu Ser Ser Ala Arg Trp Arg Arg Pro Arg Val Ala Lys Leu Ala Ser
145                 150                 155                 160

Ala Ala Ala Trp Val Leu Ser Leu Cys Met Ser Leu Pro Leu Leu Val
                165                 170                 175

Phe Ala Asp Val Gln Glu Gly Gly Thr Cys Asn Arg Leu Pro Arg Ala
            180                 185                 190

Gly Pro Gln Pro Pro Gly Gly His Arg Glu Arg Leu Ser Gly His Lys
        195                 200                 205

Ser Trp Gln Glu Lys Gly Pro Gly
    210                 215

<210> SEQ ID NO 9
<211> LENGTH: 22
<212> TYPE: DNA
<213> ORGANISM: Homo sapiens

<400> SEQUENCE: 9
ccgccagagc ttccagaagg tt                                           22

<210> SEQ ID NO 10
<211> LENGTH: 22
<212> TYPE: DNA
<213> ORGANISM: Homo sapiens

<400> SEQUENCE: 10
gctggtctgc ataagcccgt tg                                           22

<210> SEQ ID NO 11
<211> LENGTH: 23
<212> TYPE: DNA
<213> ORGANISM: Homo sapiens

<400> SEQUENCE: 11
ggcgccgtct tcatcatcta cac                                          23

<210> SEQ ID NO 12
<211> LENGTH: 22
```

<212> TYPE: DNA
<213> ORGANISM: Homo sapiens

<400> SEQUENCE: 12
ggggtggggg aggtaggaca at                                            22

<210> SEQ ID NO 13
<211> LENGTH: 23
<212> TYPE: DNA
<213> ORGANISM: Homo sapiens

<400> SEQUENCE: 13
gtcctgtctc tgtgcatgtc gct                                           23

<210> SEQ ID NO 14
<211> LENGTH: 22
<212> TYPE: DNA
<213> ORGANISM: Homo sapiens

<400> SEQUENCE: 14
caggatttgt gcccactcag cc                                            22

<210> SEQ ID NO 15
<211> LENGTH: 22
<212> TYPE: DNA
<213> ORGANISM: Homo sapiens

<400> SEQUENCE: 15
atggagcccc tgttcccagc ct                                            22

<210> SEQ ID NO 16
<211> LENGTH: 23
<212> TYPE: DNA
<213> ORGANISM: Homo sapiens

<400> SEQUENCE: 16
tgggtcctgt ctctgtgcat gtc                                           23

<210> SEQ ID NO 17
<211> LENGTH: 21
<212> TYPE: DNA
<213> ORGANISM: Homo sapiens

<400> SEQUENCE: 17
ctggtgttcg cggacgtgca g                                             21

<210> SEQ ID NO 18
<211> LENGTH: 30
<212> TYPE: DNA
<213> ORGANISM: Homo sapiens

<400> SEQUENCE: 18
tcaagcttcg atggagcccc tgttcccagc                                    30

<210> SEQ ID NO 19
<211> LENGTH: 21
<212> TYPE: DNA
<213> ORGANISM: Homo sapiens

<400> SEQUENCE: 19
cggcgcgaag aagcccagca c                                             21

<210> SEQ ID NO 20
<211> LENGTH: 19

```
<212> TYPE: DNA
<213> ORGANISM: Homo sapiens

<400> SEQUENCE: 20
ctgctgagag gcagcggcc                                             19

<210> SEQ ID NO 21
<211> LENGTH: 30
<212> TYPE: DNA
<213> ORGANISM: Homo sapiens

<400> SEQUENCE: 21
ttaggatcct cagagcaagg ccaagttgcc                                 30

<210> SEQ ID NO 22
<211> LENGTH: 21
<212> TYPE: DNA
<213> ORGANISM: Homo sapiens

<400> SEQUENCE: 22
gttgcaggta ccgccctcct g                                          21

<210> SEQ ID NO 23
<211> LENGTH: 22
<212> TYPE: DNA
<213> ORGANISM: Homo sapiens

<400> SEQUENCE: 23
cgtctgccca gagcaggacc tc                                         22

<210> SEQ ID NO 24
<211> LENGTH: 30
<212> TYPE: DNA
<213> ORGANISM: Homo sapiens

<400> SEQUENCE: 24
actggatcct cagcctgggc ctttctcctg                                 30
```